US012797202B2

(12) United States Patent
Tepic

(10) Patent No.: US 12,797,202 B2
(45) Date of Patent: Nov. 17, 2026

(54) TOTAL SHOULDER PROSTHESIS

(71) Applicant: Kyon AG, Zürich (CH)

(72) Inventor: Slobodan Tepic, Zurich (CH)

(73) Assignee: Kyon AG, Zurich (CH)

(*) Notice: Subject to any disclaimer, the term of this patent is extended or adjusted under 35 U.S.C. 154(b) by 0 days.

(21) Appl. No.: 16/603,060

(22) PCT Filed: Apr. 6, 2018

(86) PCT No.: PCT/EP2018/058847
§ 371 (c)(1),
(2) Date: Oct. 4, 2019

(87) PCT Pub. No.: WO2018/185278
PCT Pub. Date: Oct. 11, 2018

(65) Prior Publication Data

US 2020/0138585 A1 May 7, 2020

(30) Foreign Application Priority Data

Apr. 7, 2017 (EP) .................................... 17165554

(51) Int. Cl.
*A61F 2/40* (2006.01)
*A61F 2/30* (2006.01)

(52) U.S. Cl.
CPC .............. *A61F 2/40* (2013.01); *A61F 2/4003* (2013.01); *A61F 2002/3008* (2013.01); *A61F 2002/30235* (2013.01); *A61F 2002/30332* (2013.01); *A61F 2002/307* (2013.01); *A61F 2002/30784* (2013.01); *A61F 2002/3085* (2013.01); *A61F 2002/4022* (2013.01); *A61F 2002/4085* (2013.01); *A61F 2310/00023* (2013.01); *A61F 2310/00029* (2013.01); *A61F 2310/00203* (2013.01); *A61F 2310/00239* (2013.01); *A61F 2310/00407* (2013.01); *A61F 2310/00796* (2013.01)

(58) Field of Classification Search
CPC .... A61F 2/4059; A61F 2/3662; A61F 2/4003; A61F 2/40; A61F 2/4081; A61F 2/32; A61F 2/34; A61F 2002/4022; A61F 2002/4085; A61F 2002/4051
See application file for complete search history.

(56) References Cited

U.S. PATENT DOCUMENTS

| | | | |
|---|---|---|---|
| 3,815,157 | A | 6/1974 | Skorecki et al. |
| 4,693,723 | A | 9/1987 | Gabard |

(Continued)

FOREIGN PATENT DOCUMENTS

| | | | |
|---|---|---|---|
| AU | 5183801 | A | 8/2001 |
| EP | 0630624 | A1 | 12/1994 |

(Continued)

OTHER PUBLICATIONS

International Search Report cited in PCT/EP2018/058847, dated Jul. 9, 2018, 4 pages.

(Continued)

*Primary Examiner* — Marcia L Watkins
(74) *Attorney, Agent, or Firm* — Klarquist Sparkman, LLP

(57) ABSTRACT

The invention relates to a total prosthesis for the shoulder joint. It is of the socalled reverse type with a concave component in the humerus and a convex component on the scapula.

20 Claims, 13 Drawing Sheets

(56) References Cited

U.S. PATENT DOCUMENTS

| | | | | |
|---|---|---|---|---|
| 4,883,490 | A * | 11/1989 | Oh | A61F 2/34 623/22.39 |
| 5,263,988 | A * | 11/1993 | Huebner | A61F 2/32 623/22.29 |
| 5,314,488 | A * | 5/1994 | Hayashi | A61F 2/34 623/22.36 |
| 5,549,693 | A | 8/1996 | Roux et al. | |
| 5,879,404 | A * | 3/1999 | Bateman | B29C 70/68 623/22.21 |
| 6,102,951 | A | 8/2000 | Sutter et al. | |
| 6,695,884 | B1 * | 2/2004 | Townley | A61F 2/30767 623/23.29 |
| 6,863,690 | B2 * | 3/2005 | Ball | A61F 2/4059 623/19.11 |
| 7,156,879 | B1 * | 1/2007 | Albrektsson | A61F 2/3601 606/65 |
| 2004/0053199 | A1 * | 3/2004 | Minevski | A61L 27/06 433/201.1 |
| 2004/0225360 | A1 * | 11/2004 | Malone | A61F 2/446 623/17.11 |
| 2006/0184249 | A1 * | 8/2006 | Tarabishy | A61F 2/34 623/22.17 |
| 2007/0156246 | A1 | 7/2007 | Meswania et al. | |
| 2008/0109001 | A1 * | 5/2008 | Hume | A61F 2/4684 606/91 |
| 2008/0306601 | A1 * | 12/2008 | Dreyfuss | A61B 17/1778 623/19.14 |
| 2009/0076619 | A1 * | 3/2009 | Grappiolo | A61B 17/8808 623/22.4 |
| 2009/0306782 | A1 * | 12/2009 | Schwyzer | A61F 2/4003 623/19.12 |
| 2012/0213911 | A1 * | 8/2012 | Bucciotti | B22F 5/10 427/2.26 |
| 2012/0221111 | A1 * | 8/2012 | Burkhead, Jr. | A61F 2/4081 623/19.11 |
| 2013/0060345 | A1 * | 3/2013 | Tepic | A61F 2/3603 623/23.11 |
| 2013/0304225 | A1 * | 11/2013 | Komistek | A61F 2/34 623/22.16 |
| 2015/0051707 | A1 * | 2/2015 | Bresina | A61F 2/30767 623/22.2 |
| 2015/0073560 | A1 * | 3/2015 | Shavit | A61L 27/446 623/18.11 |
| 2015/0250597 | A1 * | 9/2015 | Lang | A61F 2/3609 623/22.15 |

FOREIGN PATENT DOCUMENTS

| | | | | |
|---|---|---|---|---|
| EP | 0707838 | A1 | 4/1996 | |
| EP | 0884032 | A1 | 12/1998 | |
| FR | 2103145 | A5 | 4/1972 | |
| FR | 2545352 | A1 | 11/1984 | |
| GB | 1362187 | | 7/1974 | |
| GB | 2405346 | A | 3/2005 | |
| JP | H11-000341 | A | 1/1999 | |
| JP | 2007-503861 | A | 3/2007 | |
| JP | 2007202965 | A | 8/2007 | |
| JP | 2014-534830 | A | 12/2014 | |
| WO | WO-0062718 | A1 * | 10/2000 | A61F 2/3603 |
| WO | 2007041879 | A1 | 4/2007 | |
| WO | 2013030668 | A1 | 3/2013 | |
| WO | WO2013041906 | A1 | 3/2013 | |

OTHER PUBLICATIONS

Notification of Reasons for Rejection issued in Japanese application No. 2019-539842 dated Mar. 3, 2022.

Chinese Office Action issued on May 16, 2022 in CN Application No. 2018800174565, 15 pages.

* cited by examiner

TOTAL SHOULDER PROSTHESIS

CROSS REFERENCE TO RELATED APPLICATION

This application is a 35 U.S.C. 371 National Phase Entry Application from PCT/EP2018/058847, filed Apr. 6, 2018, which claims the benefit of European Patent Application No. 17165554.1 filed on Apr. 7, 2017, the disclosures of which are incorporated herein in their entirety by reference.

FIELD OF THE INVENTION

The invention relates to a total prosthesis for the shoulder joint. It is of the so-called reverse type with a concave component in the humerus and a convex component on the scapula.

BACKGROUND

Total shoulder arthroplasty is currently the fastest growing joint replacement. This in part is due to improved clinical performance of the implants, but also due to increasing acceptance of the reverse type of the prosthesis. In the anatomic type prosthesis, the humeral head is replaced by a prosthetic head of similar size and shape, most commonly sitting on the proximal end of a humeral stem. The glenoid cavity is also replaced by an implant of very similar shape to the natural one, commonly fixed by screws and adapted for the secondary bone ingrowth.

In the reverse type prosthesis, the shape and extent of the articulation is very similar, but simply reversed: the proximal humerus now has a shallow cavity and the scapula carries a rather flat head of large radius. This shifts the center of rotation into the scapula—it is not clear if this is of help for the clinical outcomes or not, but the range of movement is generally increased.

There are still issues with the current procedures: luxations, wear of the articulation and failure of permanent anchorage to the bone.

The present invention, with its radical departure from conventional approaches, addresses most of the problems of this important orthopedic intervention. Additionally, it can shorten the surgery time and make the procedure significantly less invasive.

DESCRIPTION OF THE INVENTION

The invention discloses a total shoulder prosthesis of the reverse type. The concave component, fixed in the proximal humerus below the resection plane of the humeral head, is a deep cup, covering about 180° or more, e.g. about 180° to about 200°, of the prosthetic head fixed to the scapula. It is very similar to the acetabular cups of the total hip prosthesis and preferably fixed by press fit into reamed-out cancellous bony bed, followed by secondary stabilization by bone ingrowth.

The convex component is a spherical head very similar to that of the femoral replacement in the total hip arthroplasty. It is attached to a scapula anchor, which may be shaped as a tubular screw and inserted into the scapula through the subchondral bone of the glenoid cavity and then along the long axis of the scapula, partially cutting into all three flat bones forming the triad of the scapula.

The prosthesis of this invention offers great range of impingement-free movement, superior stability and straightforward, time-saving surgery. It is suitable for use in human and veterinary medicine.

Thus, one aspect of the present invention relates to a total shoulder prosthesis of the reverse type comprising:

(i) a concave component 300 adapted for attachment to the proximal humerus, and (ii) a convex component comprising a spherical head 200 and a bone anchor 100 adapted for attachment to the scapula, wherein the concave component 300 comprises a recess 301 adapted to receive the spherical head 200 and wherein the concave component 300 provides a coverage of at least about 180° of the spherical head 100.

A further aspect of the invention relates to a method for shoulder surgery, comprising implanting a prosthesis as described above into a subject in need thereof.

The total shoulder prosthesis of this invention places a deep, spherical articulation inside the humeral bone, with its center just proximally to its natural location even though it is of reverse type. Conventional reverse-type shoulder prosthesis place the center of rotation very proximally, with a large radius flat head affixed to the scapula. Stability of either anatomical or reverse-type prosthesis is limited by their shallow articulations. The prosthesis of this invention provides superior stability and, by its refined construction relying on the best materials and the geometry of the articulation, extremely low wear.

Anchorage of both components is unique for this joint, is surgically simplified and secure. A significant time saving in surgery is expected with lower costs of both the implants and surgical fees.

In the following, preferred embodiments of the invention are described in reference to the accompanying Figures.

BRIEF DESCRIPTION OF THE SEVERAL VIEWS OF THE DRAWINGS

FIG. 1 shows

FIG. 1*a* shows a perspective view of the scapular anchor screw 100. The cylindrical, tubular body 101 of the anchor screw carries the conical neck 102 on its distal end. Hollowed out core 103 leaves a large proportion of the bone in situ. Between the threads 104 there are numerous holes 105 facilitating rapid integration into bone and revascularization of the bone in the core of the anchor screw. Only 3 columns of the these holes are shown on this drawing, but preferably they run around the full circumference of the screw. Preferred material for the anchor screw 100 is one of titanium alloys, most preferably titanium-aluminium-niobium, which has high strength, but also exceptional biocompatibility. For improved bone integration it may be coated by porous titanium and/or hydroxy-apatite.

FIG. 1*b* shows an orthogonal view of the anchor screw 100 and the scapular head 200 fitted to the conical neck 102. At the end of the conical neck 102, the anchor screw is provided with a screwdriver recess 106. The anchor screw neck section may be cannulated to allow its insertion over a guide pin using a cannulated screwdriver. The scapular head may be made from one of suitable metal alloys, e.g. cobaltchromium, or more preferably from a high strength ceramic, e.g. alumina, zirconia or their blend.

FIG. 2 shows perspective views of the humeral cup 300. The recess 301 is adapted to receive the spherical head 200. It covers the head by at least about 180°, preferably even by up to about 190° or about 200° for greater resistance to luxation, but with still adequate range of impingement-free movement. The body 302 of the cup can be made from a biocompatible polymer such as polyether ether ketone (PEEK) and at the annular contact to the head may be provided with a ring 303, made from a reinforced material, particularly a reinforced PEEK ring, e.g. a carbon fiber reinforced PEEK ring 303. Wear of this ring when articulated with a ceramic head is extremely low. The back side of the cup, i.e. the side distal to the convex component, may be coated with a porous layer of titanium and/or hydroxyapatite. For radiographic identification, the cup may be provided with a radiographic tag, e.g. a metal ring 304 at its equator.

FIGS. 3 to 11 show a sequence of surgical steps for implantation of the shoulder prosthesis according to this invention. This sequence was made on a plastic model of a dog shoulder joint, which has a very similar anatomy to the human shoulder. The invention is equally well applicable to humans and certain animal species, dogs in particular.

FIG. 3 shows reaming of the hemispherical cavity in the humerus. The head of the humerus was removed by a planar osteotomy just above the transition from the head into the neck.

FIG. 4 shows insertion of guide pin into the scapula. The starting point is at the center of the glenoid cavity; the orientation is along the line where the three planar wings of the scapula meet. Finding the proper orientation can be aided by a minor surgical exposure of the bone behind the glenoid cavity just over its edge. Aiming at approximately 90 degrees to the glenoid cavity is an alternative.

FIG. 5 shows the first step of coring the cylindrical cut into the scapula with a short cannulated corer.

FIG. 6 shows the second step of cutting deeper into the scapula with a longer cannulated corer. The length of this cutter prevents precise guidance over the guide pin, but once the first, short cutter was used to precisely center the cut over the guide pin, this long instrument can be safely used to finish the coring.

FIG. 7 shows the view into the glenoid cavity after the coring for the implant was finished. Note the cut exiting the bone behind the glenoid subchondral bone, before it enters into the spine of the scapula.

FIG. 8 shows insertion of the scapular anchor screw. The screw is seated in the scapula by entering and exiting from the bone at multiple locations periosteal reaction of the bone along those cuts is expected to lead to a rapid and strong integration of the implant.

Figure 1A:
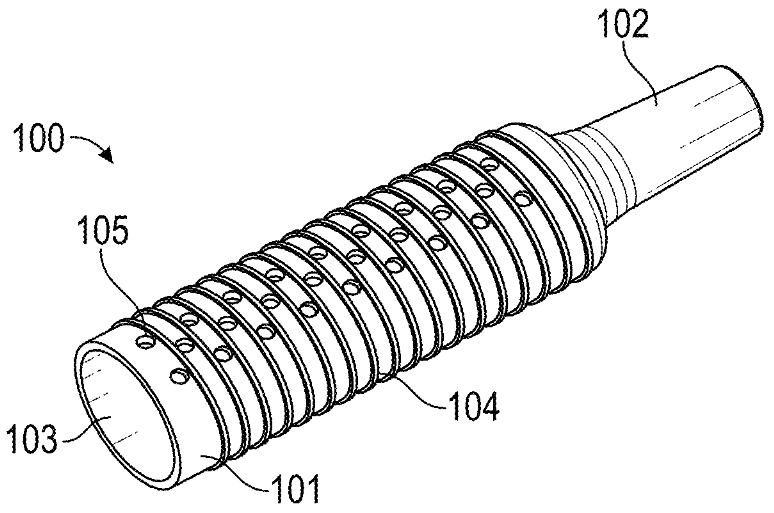
FIGS. 1*a* and 1*b* show a perspective and planar view of the scapular components of a preferred embodiment of the prosthesis according to the present invention.
Figure 1B:
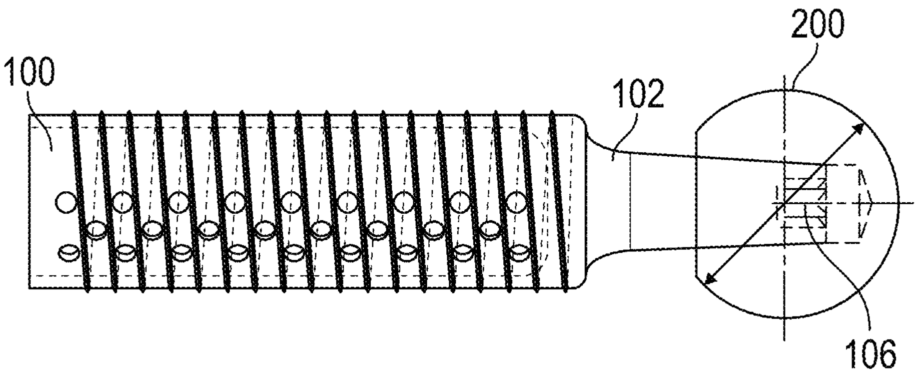
Figure 2:
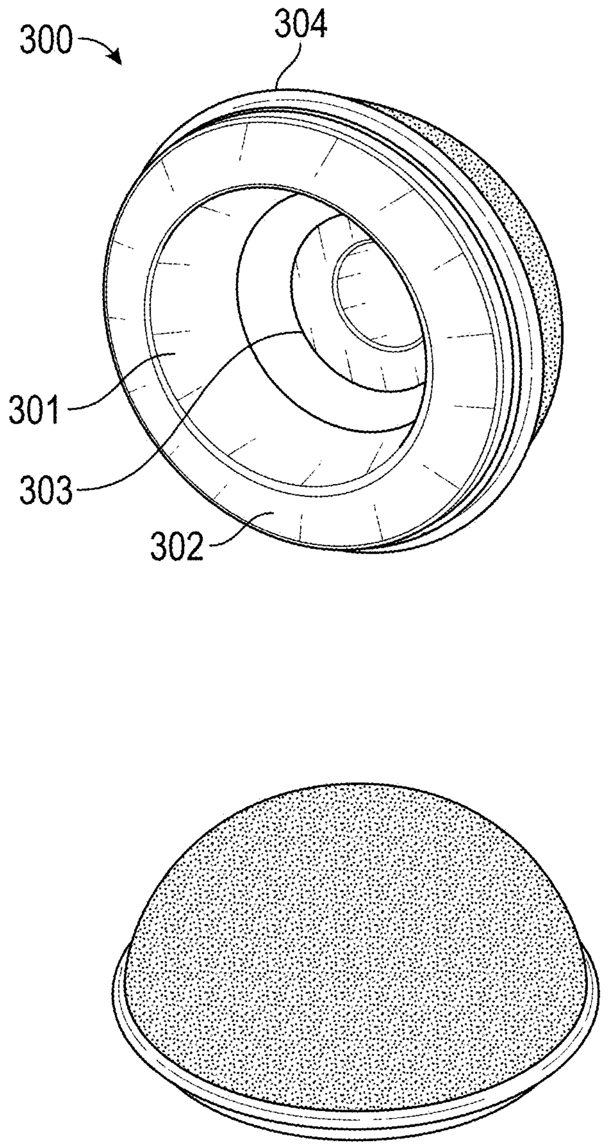
FIG. 2 shows perspective views of the humeral cup of a preferred embodiment of the prosthesis according to the present invention.
Figure 3:
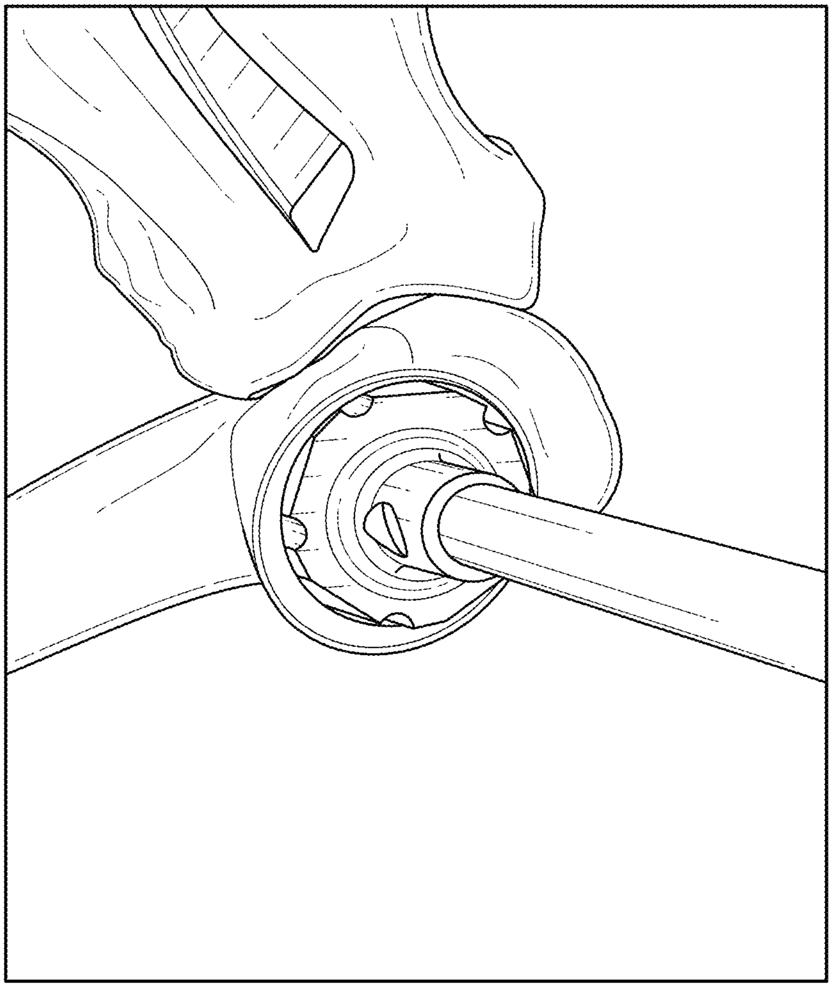
FIGS. 3 to 11 show the surgical steps of implanting the prosthesis according to the present invention.
Figure 4:
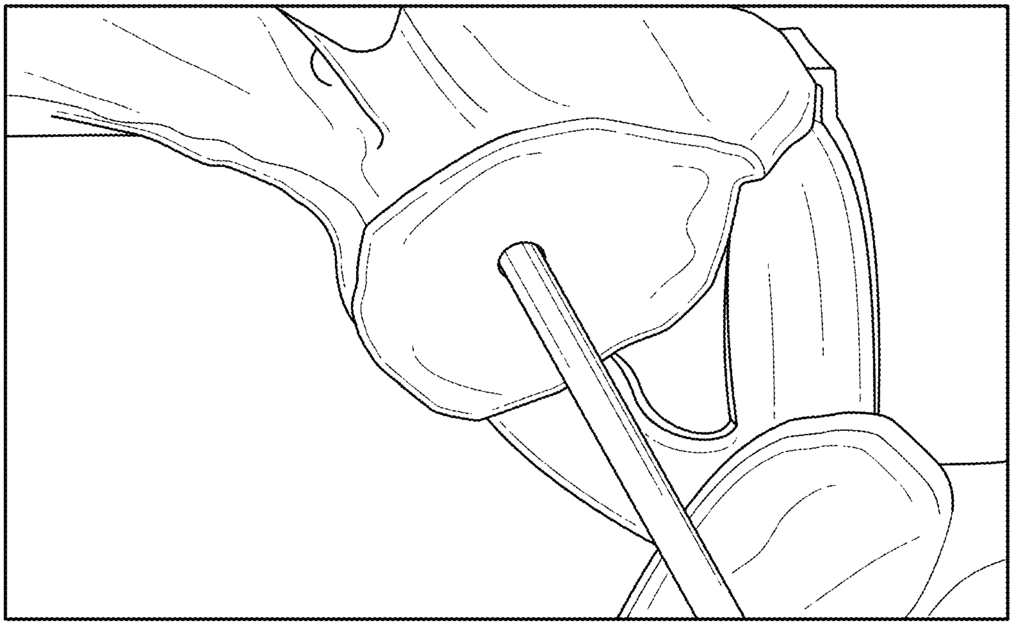
Figure 5:
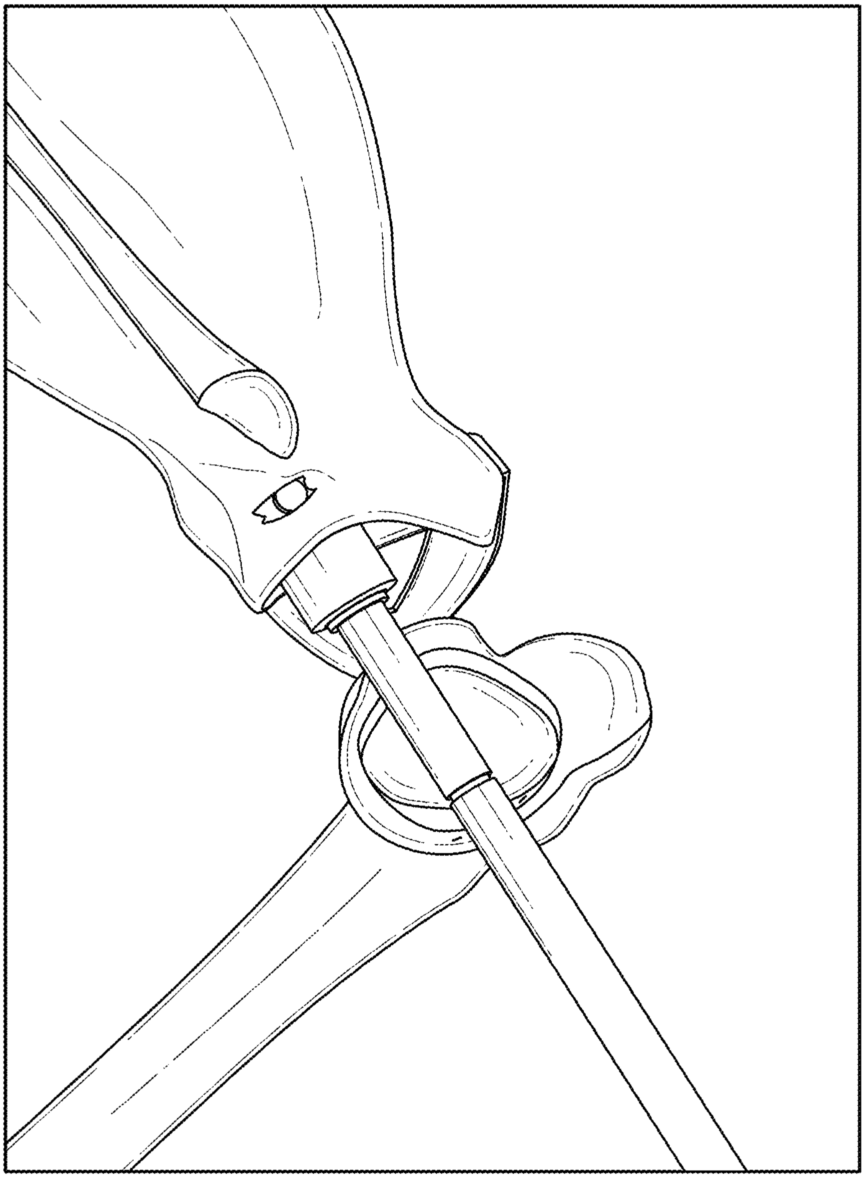
Figure 6:
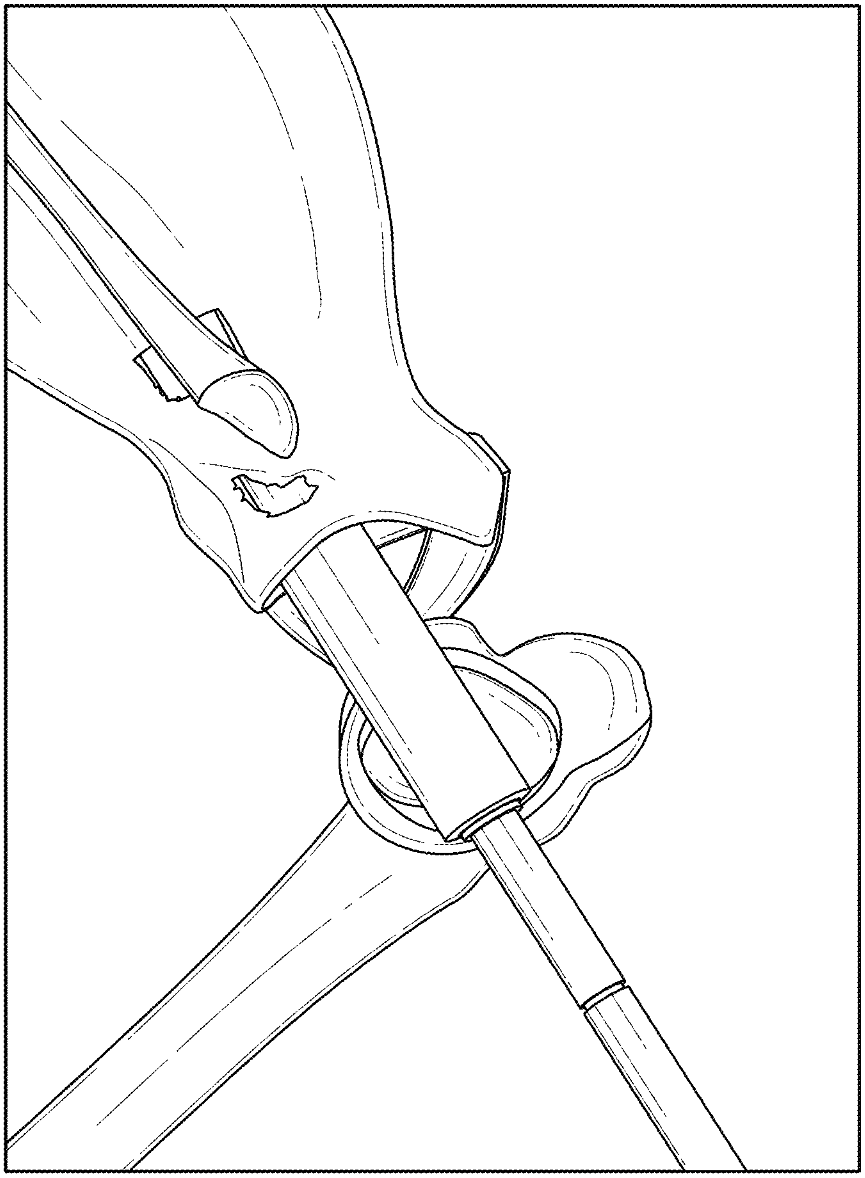
Figure 7:
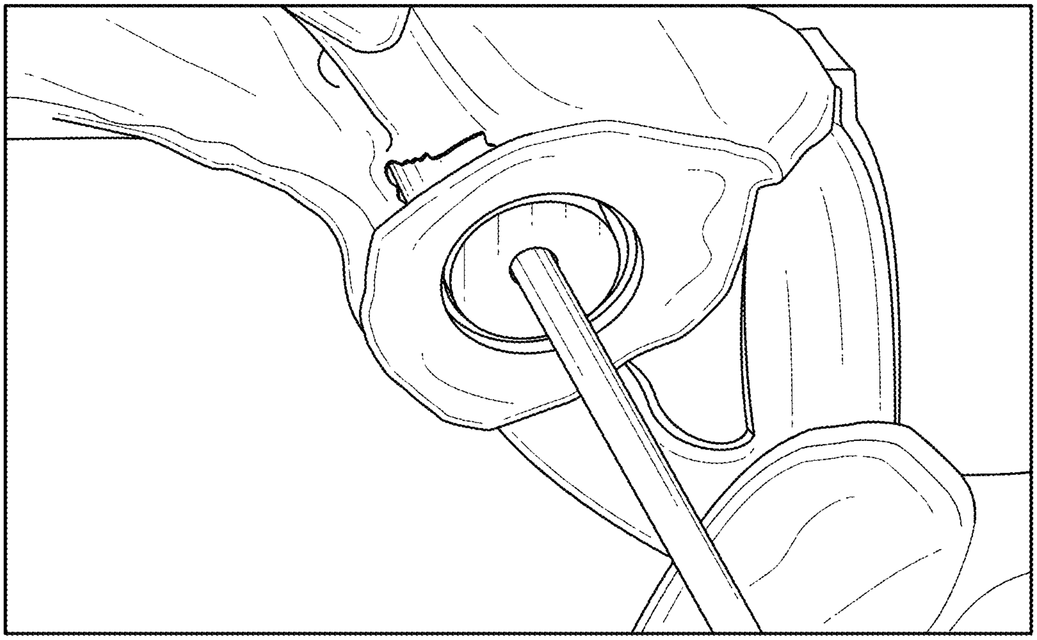
Figure 8:
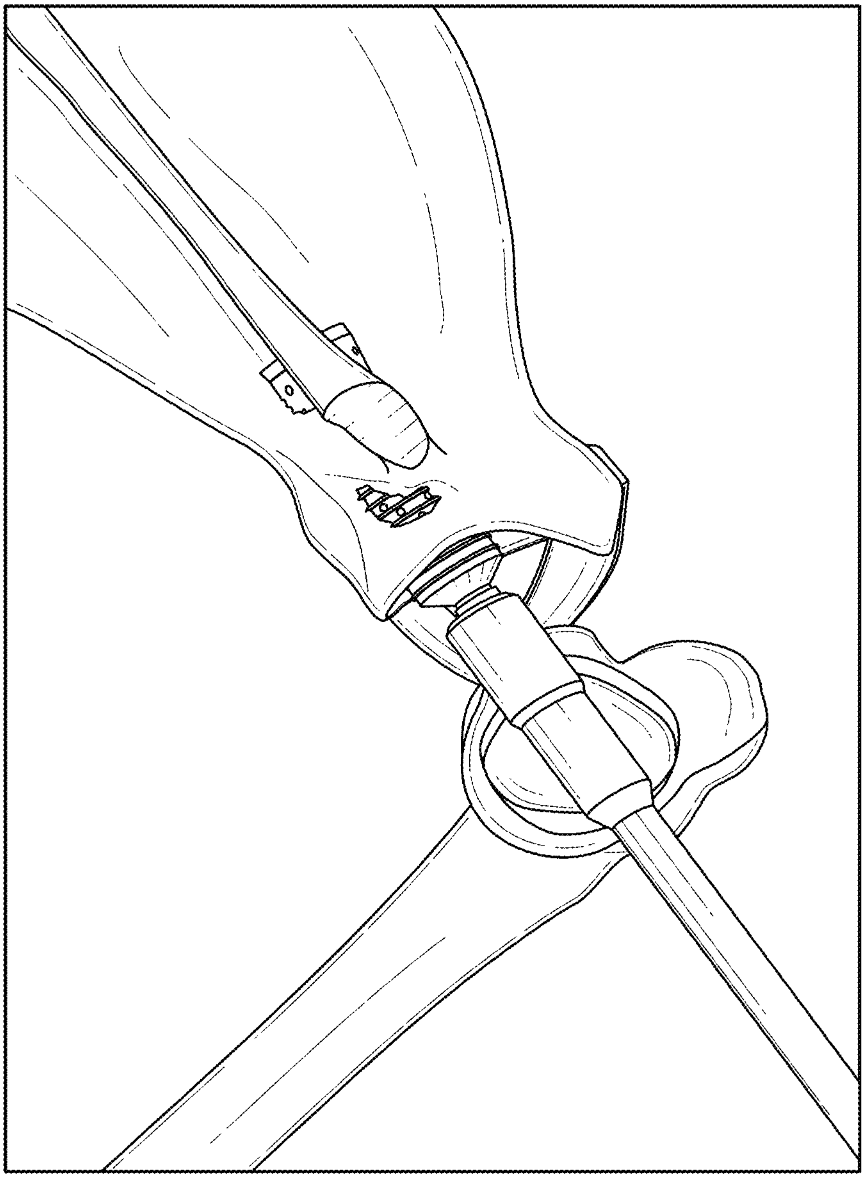
Figure 9:
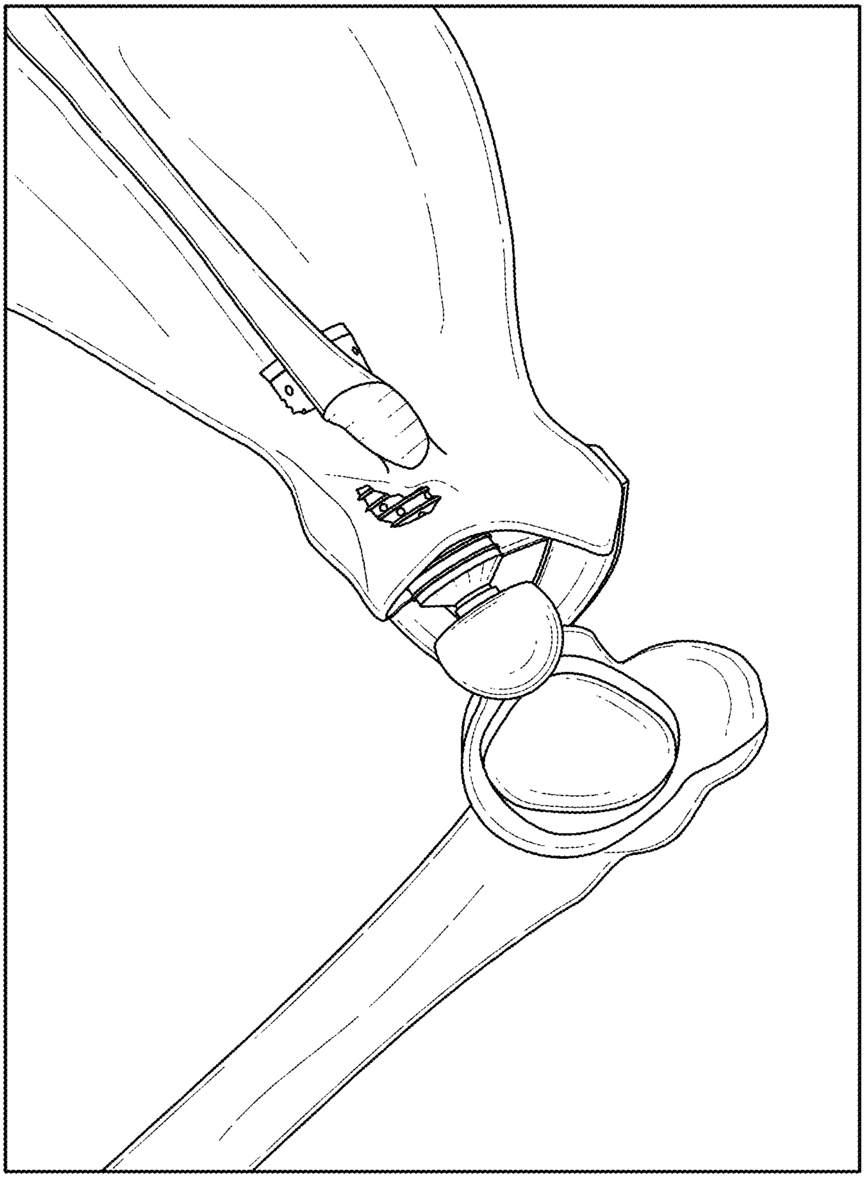

Once the screw is inserted the head of the prosthesis is attached to the anchor, FIG. 9, via precise conical fit. Length of the neck can be changed by either depth of anchor insertion or by choice of the heads with different recess depths, as is routinely done for e.g. total hip replacement.

Figure 10:
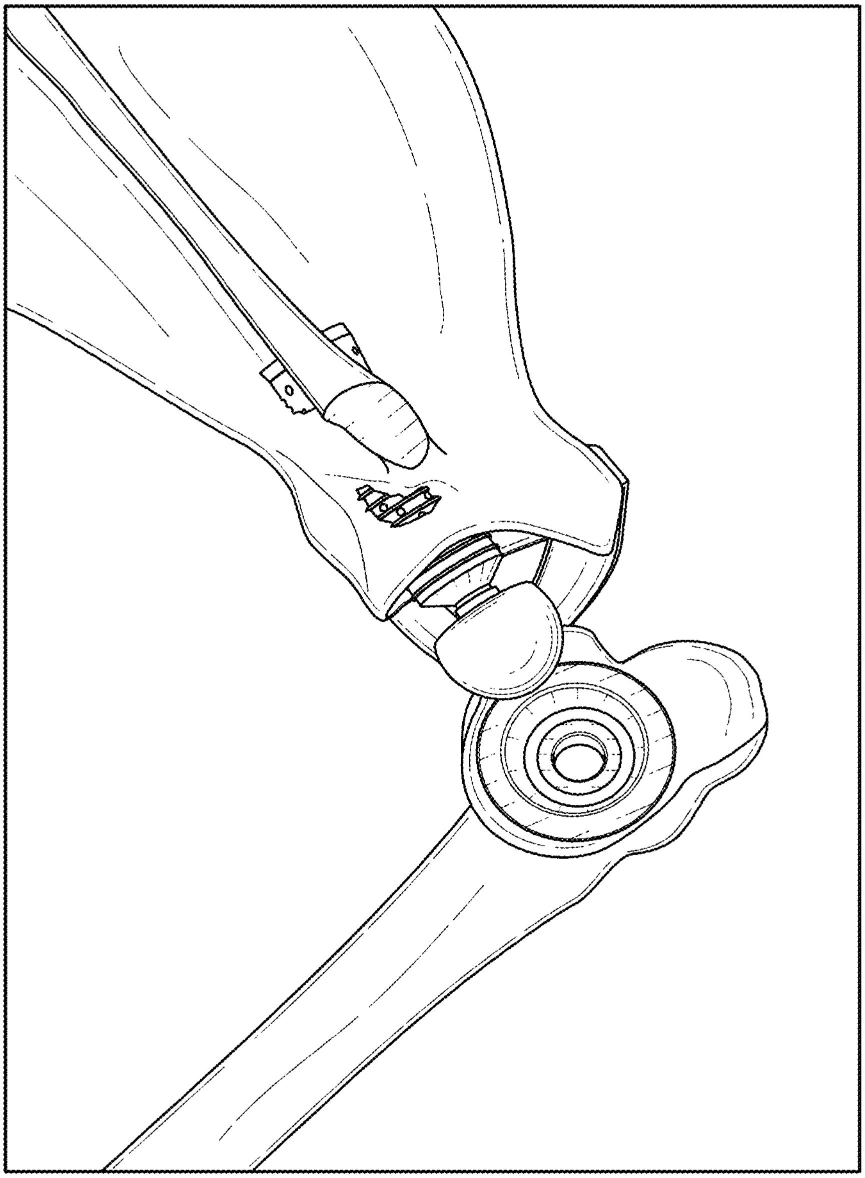

FIG. 10 shows the humeral cup inserted into its prepared cavity. This is preferably a cementless type, but an alternative is fixation of the cup by bone cement.

Figure 11:
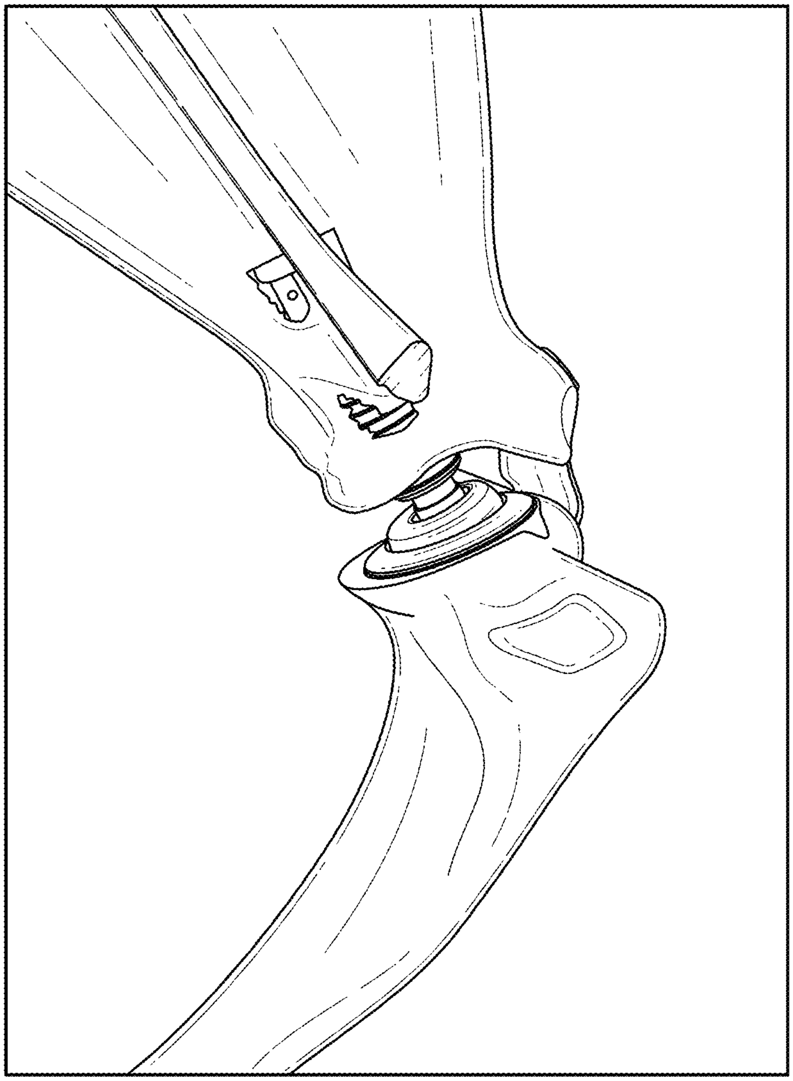

FIG. 11 shows the reduced total shoulder prosthesis. Because the neck of the scapular component is of a small diameter compared to the head diameter, the prosthesis has a very large range of impingement-free movement. There is little bending expected on the anchor indication for that is the very shallow glenoid cavity, which could not resist large variations in joint force vector.

Figure 12:
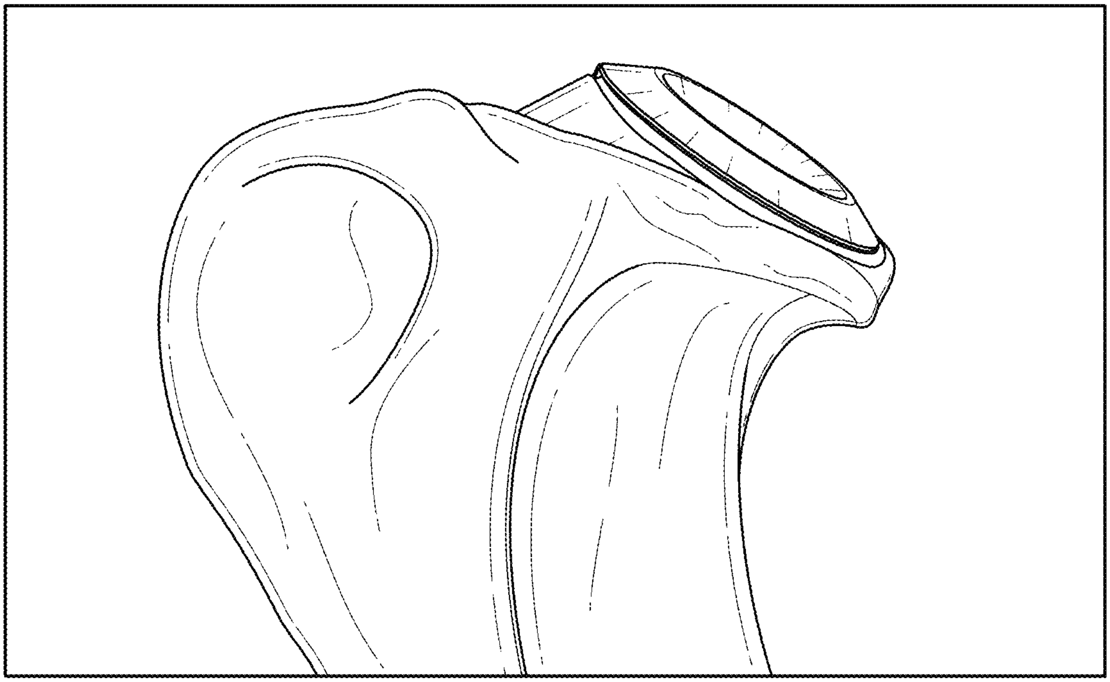
FIGS. 12 and 13 show an embodiment of a humeral cup implanted into a dog humerus.

FIG. 12 shows a tangential view of the humeral cup inserted in a dog cadaver. Quality of cancellous bone is very good in this region and a stable fixation without a conventional stem should be reliably achieved.

Figure 13:
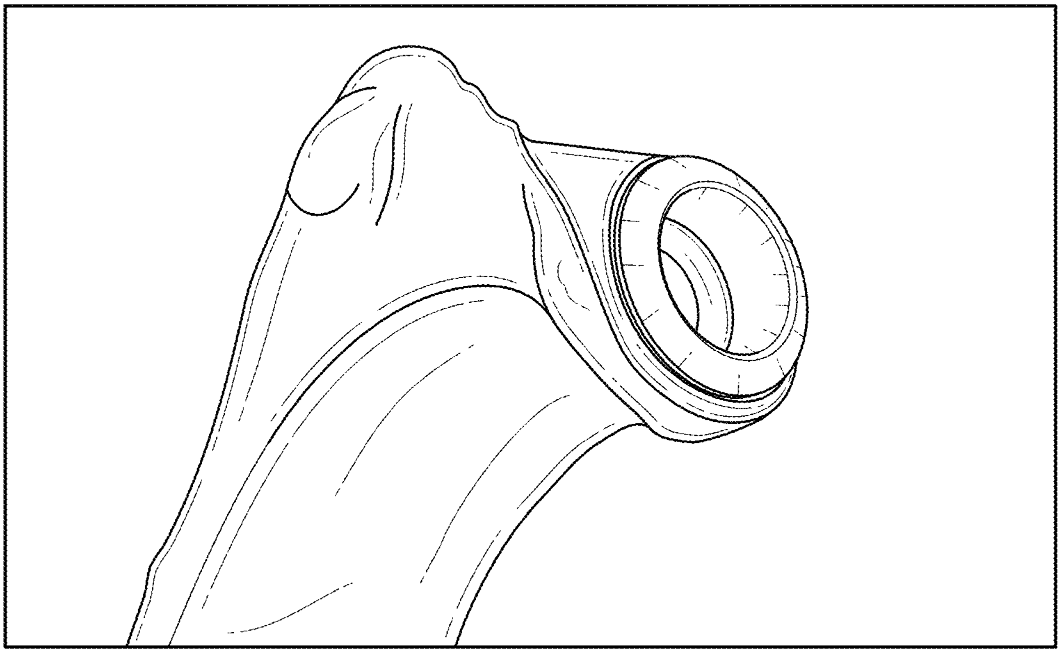

FIG. 13 is perspective view of the humeral cup demonstrating its appropriate size and placement.

The invention claimed is:

1. A total shoulder prosthesis of a reverse type comprising:

(i) a concave component adapted for attachment to a proximal humerus, and (ii) a convex component consisting of a spherical head and a bone anchor adapted for attachment to a scapula, wherein the concave component comprises a recess adapted to receive the spherical head and wherein the concave component provides a coverage of about 180° to about 200° of the spherical head, wherein the bone anchor is formed as a screw and comprises a cylindrical tubular body with threads extending around a threaded portion, wherein the bone anchor comprises a conical neck on its distal portion adapted for attachment to the spherical head and a plurality of holes, wherein the conical neck comprises a distal portion and a proximal portion, and wherein the cylindrical tubular body has a circumference, and the plurality of holes runs around the full circumference of the tubular body, wherein the bone anchor is provided with a screwdriver recess at an end of the conical neck for attachment to the spherical head, wherein the spherical head comprises a recess adapted to receive the distal portion of the conical neck, wherein the conical neck is sized such that, when the distal portion of the conical neck is received within the recess of the spherical head, the proximal portion of the conical neck is exposed from the spherical head and forms an exposed non-threaded portion of the bone anchor disposed between the threaded cylindrical tubular body and a proximal edge of the spherical head, wherein the proximal portion of the conical neck comprises a shoulder located between the threaded portion and the distal portion of the conical neck, and wherein the cylindrical tubular body is collarless and the threaded portion has a constant diameter between a proximal end of the cylindrical tubular body and the shoulder of the conical neck.

2. The prosthesis of claim 1, wherein the concave component has a body made from a biocompatible polymer.

3. The prosthesis of claim 2, wherein the biocompatible polymer is polyether ether ketone (PEEK).

4. The prosthesis of claim 1, wherein the concave component is provided with a ring made from a reinforced material in a zone of contact with the spherical head, wherein the reinforced material is a reinforced PEEK.

5. The prosthesis of claim 1, wherein the concave component has a backside which is at least partially coated with a porous layer.

6. The prosthesis of claim 1, wherein the bone anchor is made from metal.

7. The prosthesis of claim 6, wherein the metal is at least partially coated with a porous layer.

8. The prosthesis of claim 6, wherein the metal is titanium or a titanium alloy.

9. The prosthesis of claim 1, wherein said plurality of holes are positioned to produce rapid integration into bone and revascularization of the bone in the tubular body.

10. The prosthesis of claim 1, wherein said concave component adapted for attachment to a proximal humerus is suitable for attachment by press fit into a reamed-out cancellous boney bed in said humerus.

11. The prosthesis of claim 1, wherein the shoulder is configured as a shoulder fillet with a diameter that decreases in a direction extending from the cylindrical tubular body toward the distal portion of the conical neck.

12. The prosthesis of claim 11, wherein the shoulder has a largest diameter at a base of the shoulder fillet adjacent the threaded portion, and wherein the constant diameter of the threaded portion is equal to the largest diameter at the base of the shoulder fillet.

13. The prosthesis of claim 12, wherein the threads of the threaded portion of the cylindrical tubular body extend to directly adjoin the base of the shoulder fillet without an intervening unthreaded collar portion therebetween.

14. The prosthesis of claim 1, wherein the cylindrical tubular body comprises at least one thread between the shoulder and distal-most holes of the plurality of holes.

15. The prosthesis of claim 1, wherein the cylindrical tubular body is sized and shaped to enter and exit a scapula at multiple locations.

16. The prosthesis of claim 1, wherein the cylindrical tubular body comprises a proximal end portion that is thread free, the proximal end portion is located at an opposite end of the bone anchor relative to the conical neck, and the thread free proximal end portion has the same diameter as the threaded portion of the cylindrical tubular body.

17. The prosthesis of claim 16, wherein the thread free proximal end portion of the cylindrical tubular body comprises one or more holes of the plurality of holes.

18. The prosthesis of claim 1, wherein a maximum diameter of the conical neck is no greater than the constant diameter of the threaded portion of the cylindrical tubular body.

19. The prosthesis of claim 1, wherein the collarless bone anchor is configured for variable insertion depth of the bone anchor into the scapula without a collar abutting bone to delimit an insertion depth.

20. A method for shoulder surgery, comprising implanting a prosthesis according to claim 1 into a subject in need thereof.

* * * * *